US010654812B2

(12) United States Patent
Bunker

(10) Patent No.: US 10,654,812 B2
(45) Date of Patent: *May 19, 2020

(54) PROPELLANE DERIVATES AND SYNTHESIS

(71) Applicant: Kalyra Pharmaceuticals, Inc., San Diego, CA (US)

(72) Inventor: Kevin Duane Bunker, Escondido, CA (US)

(73) Assignee: Recurium IP Holdings LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/123,898

(22) PCT Filed: Mar. 5, 2015

(86) PCT No.: PCT/US2015/018886
§ 371 (c)(1),
(2) Date: Sep. 6, 2016

(87) PCT Pub. No.: WO2015/134710
PCT Pub. Date: Sep. 11, 2015

(65) Prior Publication Data
US 2017/0081295 A1  Mar. 23, 2017

Related U.S. Application Data

(60) Provisional application No. 61/949,733, filed on Mar. 7, 2014.

(51) Int. Cl.
| | |
|---|---|
| C07C 31/137 | (2006.01) |
| C07C 211/19 | (2006.01) |
| C07D 249/06 | (2006.01) |
| C07C 271/22 | (2006.01) |
| C07C 229/28 | (2006.01) |
| C07C 45/44 | (2006.01) |
| C07C 247/14 | (2006.01) |
| C07C 255/46 | (2006.01) |
| C07C 255/64 | (2006.01) |
| C07C 251/42 | (2006.01) |
| C07C 211/35 | (2006.01) |
| C07C 29/00 | (2006.01) |
| C07C 47/347 | (2006.01) |
| C07C 209/26 | (2006.01) |
| C07C 209/48 | (2006.01) |
| C07C 227/04 | (2006.01) |
| C07C 249/04 | (2006.01) |
| C07C 251/40 | (2006.01) |
| C07C 253/00 | (2006.01) |
| C07C 255/31 | (2006.01) |
| C07C 255/47 | (2006.01) |
| C07C 269/00 | (2006.01) |

(52) U.S. Cl.
CPC ............ *C07D 249/06* (2013.01); *C07C 29/00* (2013.01); *C07C 31/137* (2013.01); *C07C 45/44* (2013.01); *C07C 47/347* (2013.01); *C07C 209/26* (2013.01); *C07C 209/48* (2013.01); *C07C 211/19* (2013.01); *C07C 211/35* (2013.01); *C07C 227/04* (2013.01); *C07C 229/28* (2013.01); *C07C 247/14* (2013.01); *C07C 249/04* (2013.01); *C07C 251/40* (2013.01); *C07C 251/42* (2013.01); *C07C 253/00* (2013.01); *C07C 255/31* (2013.01); *C07C 255/46* (2013.01); *C07C 255/47* (2013.01); *C07C 255/64* (2013.01); *C07C 269/00* (2013.01); *C07C 271/22* (2013.01); *C07C 2602/38* (2017.05)

(58) Field of Classification Search
None
See application file for complete search history.

(56) References Cited

U.S. PATENT DOCUMENTS

| 5,262,417 A | 11/1993 | Gammill et al. |
|---|---|---|
| 5,404,550 A | 4/1995 | Horst |
| 5,405,550 A | 4/1995 | Michl et al. |
| 6,136,861 A | 10/2000 | Chenard |
| 9,445,025 B2 | 9/2016 | Kaiser et al. |
| 9,445,026 B2 | 9/2016 | Kobayashi et al. |
| 9,447,025 B2 | 9/2016 | Bunker |
| 9,447,026 B2 | 9/2016 | Bunker |

(Continued)

FOREIGN PATENT DOCUMENTS

| CN | 103588668 A | 2/2014 |
|---|---|---|
| CN | 103588672 A | 2/2014 |

(Continued)

OTHER PUBLICATIONS

Wiberg, Kenneth B. Reactions of [1.1.1]Propellane. J. Am. Chem. Soc. 112, (1990), 2194-2216.*
Gudipati, Murthy S. Infrared Spectra of [n]Staffanes. J. Phys. Chem. 1992, 96, 10165-10176.*
Wilberg, Kenneth B. Reactions of [1.1.1]Propellane. J. Am. Chem. Soc. 1990, 112, 2194-2216.*
Gleiter, Rolf. The Bicyclo[1.1.1]pentane Framework—an Excellent Relay for π/σ Conjugation. Angew. Chem. 1990, 102(4), 418-410.*
Barone, Veronica. NMR3J(C1,H3) Couplings in 1-X-Bicyclo[1.1.1]Pentanes. FPT-DFT and NBO Studies of Hyperconjugative Interactions and Heavy Atom Substituent Effects. Journal of Computational Chemistry. 22(14), (2001), 1615-1621.*
Database Registry Chemical Abstracts Service, Columbus, Ohio, Accession No. RN 136399-14-9, Entered STN: Sep. 28, 1991.*
Adcock, W., et al., "Transmission of polar substituent effects across the bicyclo[1.1.1]pentane ring system as monitored by $^{19}$F NMR shifts" *Magn. Reson. Chem.* (2000) 38:115-122.

(Continued)

*Primary Examiner* — Samantha L Shterengarts
(74) *Attorney, Agent, or Firm* — Knobbe, Martens, Olson & Bear, LLP

(57) ABSTRACT

Disclosed herein are compounds of the general Formula (I), and methods of synthesizing substituted bicyclo[1.1.1]pentanes. The synthetic methods described herein use a [1.1.1] propellane, a Group VIII transition metal compound, a hydride source and a reagent that can contribute a substituent to form a substituted bicyclo[1.1.1]pentane, such as a compound of the general Formula (I).

13 Claims, No Drawings

(56) References Cited

U.S. PATENT DOCUMENTS

| | | |
|---|---|---|
| 9,693,975 B2 | 7/2017 | Bunker |
| 9,724,316 B2 | 8/2017 | Bunker |
| 2004/0092531 A1 | 5/2004 | Chizh et al. |
| 2006/0052370 A1 | 3/2006 | Meyerson et al. |
| 2007/0254862 A1 | 11/2007 | Antel et al. |
| 2009/0088418 A1 | 4/2009 | Pfister et al. |
| 2010/0056553 A1 | 3/2010 | Plettenburg et al. |
| 2012/0108583 A1 | 5/2012 | Gharat et al. |
| 2012/0122846 A1 | 5/2012 | Calerwood et al. |
| 2012/0245137 A1 | 9/2012 | Pajouhesa et al. |
| 2012/0270893 A1 | 10/2012 | Dow et al. |
| 2013/0029987 A1 | 1/2013 | Bennett et al. |
| 2013/0237559 A1 | 9/2013 | Ortiz et al. |
| 2014/0275245 A1 | 9/2014 | Bunker |
| 2015/0018328 A1 | 1/2015 | Konteatis et al. |
| 2015/0246890 A1 | 9/2015 | Bahmanyar et al. |
| 2015/0297562 A1 | 10/2015 | Iinuma et al. |
| 2016/0016892 A1 | 1/2016 | Bunker |
| 2016/0075654 A1 | 3/2016 | Bunker et al. |
| 2016/0311766 A1 | 10/2016 | Bunker |
| 2016/0355462 A1 | 12/2016 | Bunker |
| 2016/0374968 A1 | 12/2016 | Bunker |
| 2018/0042871 A1 | 2/2018 | Bunker |

FOREIGN PATENT DOCUMENTS

| | | |
|---|---|---|
| EP | 0372466 A2 | 6/1990 |
| IL | 54795 | 10/1980 |
| JP | H04-502317 | 4/1992 |
| JP | 2008-120797 | 5/2008 |
| JP | 2017-501218 | 1/2017 |
| TW | 201443001 A | 11/2014 |
| WO | WO 90/06307 | 6/1990 |
| WO | WO 2000/056318 A1 | 9/2000 |
| WO | WO 2001/091736 A2 | 12/2001 |
| WO | WO 2005/063754 A1 | 7/2005 |
| WO | WO 2008/096218 | 8/2008 |
| WO | WO 2008/096218 A1 | 8/2008 |
| WO | WO 2009/153720 | 12/2009 |
| WO | WO 2012/137089 | 10/2012 |
| WO | WO 2013/024895 | 2/2013 |
| WO | WO 2013/126856 | 8/2013 |
| WO | WO 2013/131018 | 9/2013 |
| WO | WO 2014/149819 | 9/2014 |
| WO | WO 2014/169226 A2 | 10/2014 |
| WO | WO 2014/206922 A1 | 12/2014 |
| WO | WO 2015/022263 A1 | 2/2015 |
| WO | WO 2015/061247 A2 | 4/2015 |
| WO | WO 2015/089170 | 6/2015 |
| WO | WO 2015/134710 | 9/2015 |
| WO | WO 2015/157127 A1 | 10/2015 |
| WO | WO 2015/159175 A1 | 10/2015 |
| WO | WO 2015/162459 A1 | 10/2015 |
| WO | WO 2016/016370 A1 | 2/2016 |
| WO | WO 2016/044331 | 3/2016 |

OTHER PUBLICATIONS

Adcock et al., "Polar Substituent Effects in the Bicyclo[1.1.1]pentane Ring System: Acidities of 3-Substituted Bicyclo[1.1.1]pentane-1-carboxylic Acids" J.Org. Chem. (2005) 70(3):1029-1034.

Adcock, W., "A DFT-GIAO and DFT-NBO study of polar substituent effects on NMR $^{17}O$ chemical shifts in some rigid polycyclic alkanes" J. Phys. Org. Chem. (2011) 24:492-498.

Applequist, D.E., et al., "Polar Substituent Effects in 1,3-Disubstituted Bicyclo[1.1.1]pentanes" J. Org. Chem. (1982) 47:4985-4995.

Bunz et al., Chemische Berichte (1998) 121(10):1785-1790 (RN 115092-76-7 and RN 115092-79-0).

Contreras, R.H. et al., "Experimental and DFT studies on the transmission mechanisms of analogous NMR $J_{CH}$ and $J_{CC}$ couplings in 1-X- and 1-X-3-methylbicyclo[1.1.1]-pentanes" Magn. Reson. Chem. (2007) 45:572-577.

Hassner, A. "e-EROS Encyclopedia of Reagents for Organic Chemistry" (2005) 1-6 (John Wiley & Sons, Ltd., Chichester) (RN 351882-60-5 and RN351882-61-6).

Janecki, T., et al., "[n]Staffanes with Terminal Nitrile and Isonitrile Functionalities and their Metal Complexes" Collect. Czech. Chem. Commun. (1993) 83:89-104.

Pätzel, M., et al., "3-Aminobicyclo[1.1.1]pentane-1-carboxylic Acid Derivatives: Synthesis and Incorporation into Peptides" Eur. J. Org. Chem. (2004):493-498.

Toops et al., "Efficient Synthesis of 1-(Trialkylstannyl)- and 1-(Triarylstannyl)bicyclo[1.1.1]pentanes" J. Org. Chem. (1993) 58:6505-6508.

Wang et al., "The Oral Analgesic Efficacy of Bicifadine Hydrochloride in Postoperative Pain" J. Clin. Pharm. (1982) 22(4):160-164.

Zehnder et al., "Optimization of Potent, Selective, and Orally Bioavailable Pyrrolodinopyrimidine-Containing Inhibitors o Heat Shock Protein 90. Identification of Development Candidate 2-Amino-4-{4-chloro-2-[2-(4-fluoro-1H-pyrazol-1-yl)ethoxy]-6-methylphenyl}-N-(2,2-difluoropropyl)-5,7-dihydro-6H-pyrrolo[3,4-d]pyrimidine-6-carboxamidef" J. Med. Chem. (2011) 54:3368-3385.

Adcock et al., "Computation and analysis of $^{19}F$ substituent chemical shifts of some bridgehead-substituted polycyclic alkyl fluorides" Magnetic Resonance in Chemistry (2003) 41:503-508.

CAS Reg. No. 1046861-73-7, entered Sep. 5, 2008.

Office Action dated Feb. 2, 2018 for CN Application No. 201580020861.9, filed Mar. 5, 2015.

Adcock, W. et al. (1992) Transmission of Polar substituent effects through the Bicyclo[1.1.1]pentane Ring System as monitored by $^{19}F$ NMR shifts. Tetrahedron Letters, 33(48):7397-7398.

Alekseenko et al. (2012) An improved synthesis of 2-, 3-, and 4-(trifluoromethyl)cyclohexylamines. Synthesis. 44:2739-2742.

CAS Reg No. 1219538-79-0, STN Entry Date: Apr. 19, 2010.

CAS Reg No. 1219538-81-4, STN Entry Date: Apr. 19, 2010.

CAS Reg No. 1219538-83-6, STN Entry Date: Apr. 19, 2010.

CAS Reg. No. 130974-28-6, STN Entry Date Dec. 14, 1990.

Della, E.W. (1970) Fluorine-19 chemical shits in saturated systems. Australian journal of Chemistry. 23(12):2421-2426.

Radchenko, et al. (2010) Cyclobutane-derived diamines: synthesis and molecular structure. Journal of Organic Chemistry. 75:5941-5952.

Communication pursuant to Article 94(3) EPC, dated Apr. 12, 2019 for EP Application No. 15757721.4, filed Mar. 5, 2015.

Office Action dated Feb. 12, 2019 for JP Application No. 2016-573684, filed Mar. 5, 2015.

Office Action dated Nov. 9, 2018 for TW Application No. 104107323, filed Mar. 6, 2015.

Whitney et al. (1970) Antiviral agents. I. Bicyclo[2.2.2]octan- and -oct-2-enamines. Journal of Medicinal Chemistry. 13(2):254-260.

Fluck, E., "New Notations In the Periodic Table" Pure & Applied Chemistry (1988) 60(3):432-436.

IUPAC Periodic Table of the Elements (2011).

Wiberg et al., "Reactions of [1.1.1] Propellane" J. Am. Chem. Soc. (1990) 112(6):2194-2216.

Extended European Search Report dated Oct. 5, 2017 for EP Application No. 15757721.4. filed Mar. 5, 2015.

Barker et al., "Fe(III)/NaBH$_4$-mediated free radical hydrofluorination of unactivated alkenes" J. Am. Chem. Soc. (2012) 134(33):13588-13591.

Bunker et al., "Scalable Synthesis of 1-Bicyclo [1.1.1] pentylamine via a Hydrohydrazination Reaction" Org. Lett. (2011) 13(17):4746-4748.

Carey, "Organic Chemistry, $2^{nd}$ Edition" pp. 328-331 (McGraw-Hill College 1992).

Harvey et al., "The Cleavage of sym-Diphenyldisiloxane by Organometallic Compounds" J. Am. Chem. Soc. (1957) 79(6):1437-1439.

Ishikawa et al., "Total synthesis of vinblastine, vincristine, related natural products, and key structural analogues" J. Am. Chem. Soc. (2009) 131(13):4904-4916.

Keinan et al., "Silicon hydrides and molybdenum(0) catalyst: a novel approach for conjugate reduction of α,β-unsaturated carbonyl compounds" J. Org. Chem. (1987) 52(12):2576-2580.

(56) References Cited

OTHER PUBLICATIONS

Larock, "Comprehensive Organic Transformations: A Guide to Functional Group Preparations, 2$^{nd}$ Edition" (John Wiley & Sons, Inc. 1999) Table of Contents only.

Leggans et al., "Iron (III)/NaBH$_4$-mediated additions to unactivated alkenes: synthesis of novel 20'-vinblastine analogues" *Org. Lett.* (2012) 14(6):1428-1431.

Levin et al., "Bicyclo[1.1.1]pentanes, [n]Staffanes,[1.1.1]Propellanes, and Tricyclo[2.1 0.0$^{2,5}$]pentanes" *Chem. Rev.* (2000) 100(1):169-234.

Lo et al., "A practical and catalytic reductive olefin coupling" *J. Am. Chem. Soc.* (2014) 136(4):1304-1307.

Lynch et al., "[1.1.1]Propellane:(Tricyclo1.1.1.0$^{1,3}$Pentane)" *Org. Synth.* (1998) 75:98-105.

McMurry, "Organic Chemistry, 5$^{th}$ Edition" pp. 398 and 408 (Brooks Cole 2000).

Semmler et al., "Tetracyclo [5.1.0.0$^{1,6}$.0$^{2,7}$] octane, a [1.1.1] propellane derivative, and a new route to the parent hydrocarbon" *J. Am. Chem. Soc.* (1985) 107(22):6410-6411.

Shtarev et al., "Partially bridge-fluorinated dimethyl bicyclo[1.1.1]pentane-1,3-dicarboxylates: Preparation and NMR spectra" *J. Am. Chem. Soc.* (2001) 123(15):3484-3492.

Smith et al., "March's Advanced Organic Chemistry: Reactions, Mechanisms, and Structure, 6$^{th}$ Edition" (John Wiley & Sons, Inc. 2007) Table of Contents only.

Streitwieser et al., "Introduction to Organic Chemistry, 2$^{nd}$ Edition" pp. 169-171 (Macmillan Library Reference 1981).

Wiberg et al., "The reaction of 3-bromocyclobutane-1-methyl bromide with sodium: bicyclo[1.1.1]pentane" *Tetrahedron Lett.* (1964) 5(10):531-534.

Wiberg et al., "[1.1.1] Propellane" *J. Am. Chem. Soc.* (1982) 104(19):5239-5240.

International Search Report and Written Opinion dated Jun. 8, 2015 for PCT Application No. PCT/US2015/18886, filed Mar. 5, 2015.

International Preliminary Report on Patentability dated May 11, 2016 for PCT Application No. PCT/US2015/18886, filed Mar. 5, 2015.

CAS RN 130682-55-2, Entered STN: Nov. 30, 1990.

CAS RN 1230133-71-7, Entered STN: Jul. 11, 2010.

Office Action dated Aug. 19, 2019 for CN Application No. 201580020861.9, filed Mar. 5, 2015.

Examination Report dated Sep. 27, 2018 for IN Application No. 201617029511, filed Aug. 30, 2016.

Hearing Notice dated Nov. 22, 2019 for IN Application No. 201617029511, filed Aug. 30, 2016.

Notice of Final Decision of Rejection dated Nov. 5, 2019 for JP Application No. 2016-573684, filed Sep. 6, 2016.

Gasper et al., "Cobalt Catalyzed Functionalization of Unactivated Alkenes: Regioselective Reductive C—C Bond Forming Reactions" J. Am. Chem. Soc. (2009) 131:13214-13215.

Waser et al., "Hyrdazines and Azides via the Metal-Catalyzed Hydrohydrazination and Hydroazidation of Olefins" J. Am. Chem. Soc. (2006) 128:11693-11712.

* cited by examiner

PROPELLANE DERIVATES AND SYNTHESIS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present disclosure relates to synthetic organic chemistry, and in particular to [1.1.1]-bicyclopentane-based compounds (propellane derivatives) and their synthesis.

Description

There is significant need for new categories of small organic molecules useful as reagents in synthetic organic chemistry. Although it has been estimated that there are $10^{60}$ possible small carbon-containing molecules, only a tiny fraction of those can be effectively and efficiently synthesized using known reactions and readily-available starting materials (or "building blocks"). New building blocks or more efficient methods of synthesizing known but expensive building blocks could expand the chemical space available for exploration, for example, in areas such as pharmaceuticals, agricultural chemistry, polymers, advanced materials, and many other areas of endeavor.

One structural motif that is highly under-represented in synthetic organic chemistry is bicyclo[1.1.1]pentane (BCP) having the structure:

BCP

This is largely due to the difficulty, high cost, and low yields of BCP and its derivatives using known synthetic schemes. Although BCP has been the subject of some experimentation as a structural motif in pharmaceuticals, polymers, liquid crystal displays, high energy density materials, nanoparticles or molecular rods, macrocycles, organometallic complexes, and physical organic chemistry, compounds having a BCP structure have yet to be commercialized in those fields. In short, commercial use of BCPs has been hampered by availability and cost of reagents.

SUMMARY

Some embodiments disclosed herein relate to a method for preparing a substituted bicyclo[1.1.1]pentane compound that can include combining [1.1.1]propellane; a Group VIII transition metal compound; a hydride source; and a reagent capable of contributing all or a part of a substituent group such that bicyclo[1.1.1]pentane is substituted with the substituent group.

Some embodiments described herein relate to using a method described herein to obtain a compound of Formula (I), or a salt thereof.

Some embodiments described herein relate to a compound of Formula (I), or a salt thereof.

DETAILED DESCRIPTION

Bicyclo[1.1.1]pentanes are remarkably stable, despite being highly ring-strained. The first example of an isolated bicyclo[1.1.1]pentane was reported by Wiberg in 1964 (Wiberg et al. *Tetrahedron Lett.* 1964, 531-4). However, development of the bicyclo[1.1.1]pentane field was slow due to the difficult and low yielding chemistry. Some twenty years passed before a more productive route into BCPs was discovered by Wiberg (Wiberg et al. *J. Am. Chem. Soc.* 1982, 104, 5239-40) and further developed by Sziemes (Semmler et al. *J. Am. Chem. Soc.* 1985, 107, 6410-11) that utilized the highly ring-strained [1.1.1]propellane as a starting material.

Bicyclo[1.1.1]pentane has unique properties, including shape (sterics) and polarity (electronics) where the high ring-strain creates an electron withdrawing effect for substituents on the bridgehead carbons. For example, 1-bicyclo[1.1.1]pentyl amine is significantly less basic compared to tert-butylamine (pKa of the conjugate acid is 8.6 for 1-bicyclo[1.1.1]pentyl amine vs. 11.0 for tBuNH$_2$). Likewise, 1-carboxybicyclo[1.1.1]pentane is more acidic than pivalic acid (pKa of 4.09 for 1-carboxybicyclo[1.1.1]pentane vs. 5.05 for pivalic acid). These and other properties suggest that BCPs may find significant application as organic chemistry building blocks. Nevertheless, despite advances in synthesis of a few BCPs (see, e.g., Bunker et al., *Org. Lett.* 2011, 13, 4746-4748), there is a need for additional BCP building blocks and for more cost-effective syntheses for known BCP-based compounds.

Abbreviations

As used herein, the following terminology is defined as indicated:

| TERM | DEFINITION |
| --- | --- |
| EtOAc | ethyl acetate |
| THF | tetrahydrofuran |
| NMP | N-methyl-2-pyrrolidone |
| DMF | dimethylformamide |
| DMSO | dimethylsulfoxide |
| MTBE | methyl(tert-butyl)ether |

Definitions

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, sulfenyl, sulfinyl, sulfonyl, haloalkyl, haloalkoxy, an amino, a mono-substituted amino group and a di-substituted amino group.

As used herein. "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl, and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl, and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl, and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 3 to 10 atoms in the ring(s) or 3 to 8 atoms in the ring(s). When composed of two or more rings, the rings may be joined together in a fused, bridged or spiro fashion. A cycloalkynyl group may be unsubstituted or substituted.

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4- thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicylylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group

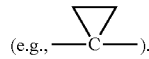

(e.g., —C—).

The term "carbonyl" used herein refers to C═O (i.e. carbon double bonded to oxygen).

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl, and acryl. An acyl may be substituted or unsubstituted.

The term "amino" used herein refers —NH$_2$.

A "mono-substituted amino" group refers to a "—NHR" group in which R can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

The term "halogen atom" or "halogen" as used herein, means any one of the radio-stable atoms of column 7 of the Periodic Table of the Elements, such as, fluorine, chlorine, bromine and iodine.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "alkoxyalkyl" refers to an alkoxy group connected, as a substituent, via a lower alkylene group. Examples include alkyl-O—(CH$_2$)n-, wherein n is an integer in the range of 1 to 6.

As used herein, "acylalkyl" refers to an acyl connected, as a substituent, via a lower alkylene group. Examples include aryl-C(═O)—(CH$_2$)n- and heteroaryl-C(═O)—(CH$_2$)n-, where n is an integer in the range of 1 to 6. An acylalkyl may be substituted or unsubstituted.

As used herein, "aminoalkyl" refers to an optionally substituted amino group connected, as a substituent, via a lower alkylene group. Examples include H$_2$N—(CH$_2$)n-, (CH$_3$)$_2$N—(CH$_2$)n- and (CH$_3$)(phenyl)N—(CH$_2$)n-, wherein n is an integer in the range of 1 to 6.

As used herein, "arylthio" refers to RS—, in which R is an aryl, such as, but not limited to, phenyl. An arylthio may be substituted or unsubstituted.

As used herein, "alkylthio" refers to a "—SR" group, in which R is alkyl, for example a C$_{1-6}$ alkyl. An alkylthio may be substituted or unsubstituted.

As used herein. "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfonyl" group refers to an "SO$_2$R" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

Where a range of values is provided, it is understood that the upper and lower limit, and each intervening value between the upper and lower limit of the range is encompassed within the embodiments.

Methods

Some embodiments disclosed herein relate to a method for preparing a substituted bicyclo[1.1.1]pentane compound that can include combining [1.1.1]propellane; a Group VIII transition metal compound; a hydride source; and a reagent capable of contributing all or a part of a substituent group such that bicyclo[1.1.1]pentane is substituted with the substituent group.

As described herein, functionalized bicyclo[1.1.1]pentanes can be prepared from [1.1.1]propellane using an iron-based compound. Although an iron-mediated reaction process has been shown to be successful in the reactions of olefins as described in Leggans et al., *Org. Lett.*, 2012, 14(6), 1428-1431, Ishikawa, H., et al., *J. Am. Chem. Soc.* 2009, 131, 4904-4916, Barker, T. J. et al., *J. Am. Chem. Soc.* 2012, 134, 13588-13591 and Lo et al., *J. Am. Chem. Soc.*, 2014, 136(4), 1304-1307, which is hereby incorporated by reference in its entirety, no iron-mediated (or Group VIII transition-metal-mediated) process is known for adding a hydride to and a functionalizing [1.1.1]propellane to yield a functionalized bicyclo[1.1.1]pentane.

A general synthetic route for preparing a substituted bicyclo[1.1.1]pentane compound is shown in Schemes 1 and 2, and described herein. The route shown and described herein is illustrative only and is not intended, nor is to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

[1.1.1]propellane

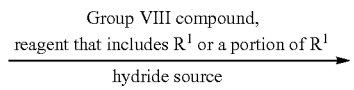

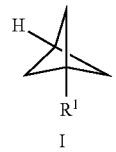
I

As shown in Scheme 1, the hydride source contributes the shown hydrogen and the reagent contributes $R^1$ or a portion of $R^1$ to the substituted bicyclo[1.1.1]pentane compound. As provided herein, various Group VIII compounds, reagents and hydride sources can be used to form a substituted bicyclo[1.1.1]pentane compound.

Propellane can be prepared via various methods. Suitable methods are described by Shtarev et al., *J. Am. Chem. Soc.* 2001, 123, 3484-3492 and Lynch et al., *Org. Synth.* 1998, 75, 98-105, which are hereby incorporated by reference in their entirety. One example of a suitable method is shown in Scheme 2.

Scheme 2

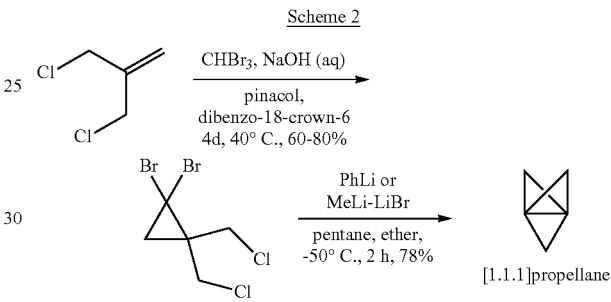

Metal-Compounds

Those skilled in the art understand that Group VIII includes the following elements: iron, ruthenium, osmium and hassium. In some embodiments, the Group VIII transition metal compound can be an iron-based transition metal compound. The oxidation state of the transition metal compound can vary. For example, in some embodiments, the oxidation state of iron can be Fe(II), such that the Group VIII transition metal compound is a Fe(II)-based transition metal compound. In other embodiments, the oxidation state of iron can be Fe(III), such that the Group VIII transition metal compound is a Fe(III)-based transition metal compound. The Group VIII transition metal compound can be a salt, a solvate (including mono- and per-solvates) or a hydrate (including mono- and per-hydrates).

In some embodiments, the Group VIII transition metal compound can include one or more ligands attached and/or coordinated to the Group VIII metal, such that the Group VIII transition metal compound is a Group VIII transition metal complex. As used herein, the term "ligand" is used herein in its ordinary sense as understood by those skilled in the art, and refers to a group bound to a central atom in a chelate or a coordination compound. Examples of suitable ligands, include but are not limited to, bathophenanthroline, phthalocyanine. N,N,N',N'-tetramethylethylenediamine, 5,10,15,20-tetrakis(pentafluorophenyl)porphyrin, tricyclohexylphosphine, bis(diphenylphosphinyl)hexane, ethylenebis(diphenylphosphine), N,N'-ethylenebis(salicylimine), benzoin and acetylacetonate. In some embodiments, more than one ligand can be present in the Group VIII transition metal complex. In some embodiments, the Group VIII transition metal complex can be an iron-based transition metal complex.

The amount of the Group VIII transition metal compound used in a method described herein can vary. In some embodiments, the Group VIII transition metal compound can be present in a stoichiometric amount. In other embodiments, the Group VIII transition metal compound can be present in a catalytic amount. In still other embodiments, the Group VIII transition metal compound can be present in an excess amount. Examples of suitable Group VIII transition metal compounds include the following: iron(III) oxalate, iron(III) sulfate, iron(III) nitrate, iron(III) acetylacetonate, iron(III) chloride, iron(II) perchlorate, iron(II) phthalocyanine, iron(II) acetate, iron(II)chloride, and iron(II) tetrafluoroborate. The Group VIII transition metal compounds are commercially available and/or can be prepared using methods known to those skilled in the art.

In some embodiments, the Group VIII transition metal compound (such as iron transition metal compound) can be present in the range of 10 mol % to 70 mol %. In some embodiments, the Group VIII transition metal compound (such as iron transition metal compound) can be present in the range of 20 mol % to 60 mol %. In some embodiments, the Group VIII transition metal compound (such as iron transition metal compound) can be present in the range of 30 mol % to 50 mol %. In some embodiments, the Group VIII transition metal compound (such as iron transition metal compound) can be present in the amount of about 30 mol %. In some embodiments, the Group VIII transition metal compound (such as iron transition metal compound) can be present in the amount of about 50 mol %.

Reagents

Various reagents can be used to contribute all or a part of a substituent group to the bicyclo[1.1.1]pentane compound. In some embodiments, the reagent can function as an electrophile and can trap a nucleophile. In other embodiments, the reagent can function as a radical trap of a carbon radical species to provide the substituted BCP.

In some embodiments, the reagent capable of contributing all or a part of a substituent group can have the structure $LG^1$-$R^1$, wherein $R^1$ attaches to a carbon of [1.1.1]propellane and $LG^1$ is a leaving group.

As used herein, "leaving group" refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, sulfonyls, and halogens (e.g., I, Br, and Cl). Non-limiting characteristics and examples of leaving groups can be found, for example in *Organic Chemistry*, $2^{nd}$ ed., Francis Carey (1992), pages 328-331; *Introduction to Organic Chemistry*, $2^{nd}$ ed., Andrew Streitwieser and Clayton Heathcock (1981), pages 169-171; and *Organic Chemistry*, $5^{th}$ ed., John McMurry (2000), pages 398 and 408; all of which are incorporated herein by reference for the limited purpose of disclosing characteristics and examples of leaving groups.

In some embodiments, $LG^1$ can be an optionally substituted sulfonyl, an optionally substituted phosphonate, an alkali metal or a transition metal. Various of optionally substituted sulfonyls and optionally substituted phosphonate are suitable. In some embodiments, the optionally substituted sulfonyl can be an optionally substituted tosyl. In some embodiments, the optionally substituted phosphonate can be an optionally substituted di(alkyl)cyanophosphonate (for example, di(ethyl)cyanophosphonate).

A non-limiting list of examples of the reagents having the structure $LG^1$-$R^1$ include tosyl azide, sulfonyl azide, lithium azide, sodium azide, potassium azide, cesium azide, zinc azide, tosyl cyanide, tosyl chloride, potassium thiocyanate, potassium cyanate, sodium nitrite, (E)-(phenylsulfonyl)methanal O-benzyl oxime, (E)-N-(benzyloxy)-1-(phenylsulfonyl)methanimidoyl cyanide, diethyl phosphorocyanidate, tert-butylisocyanate, and an optionally substituted sulfonyl oxime.

In other embodiments, the reagent capable of contributing all or a part of a substituent group can have the structure $R^{1A}$-$R^{1B}$, wherein $R^{1B}$ attaches to a carbon of propellane and undergoes a further transformation to form $R^1$, and $R^{1A}$ forms a byproduct. An example of $R^{1A}$-$R^{1B}$ is molecular oxygen. One oxygen atom of molecular oxygen attached to a carbon of [1.1.1]propellane and the other oxygen forms an oxide byproduct (e.g., silanoxy byproduct). A further example of a reagent capable of contributing all or a part of a substituent group having the structure $R^{1A}$-$R^{1B}$ is an optionally substituted oxaziridine.

In still other embodiments, the reagent capable of contributing all or a part of a substituent group can have the structure $R^1$. For these reagents, all the atoms of the reagent can add to a carbon of [1.1.1]propellane to form the substituted BCP. An example of this type of reagent is 2,2,6,6-tetramethyl-1-piperidinyloxy (TEMPO).

In yet still other embodiments, the reagent capable of contributing all or a part of a substituent group can have the structure of an optionally substituted $R^1$—$C_{2-10}$ alkenyl. In some embodiments, $R^1$—$C_{2-10}$ alkenyl can be unsubstituted. In other embodiments, $R^1$—$C_{2-10}$ alkenyl can be substituted. In some embodiments, the reagent capable of contributing all or a part of a substituent group can have the structure of an optionally substituted $R^1$—$C_{2-6}$ alkenyl Hydride Sources Various reagents can be used to donate a hydrogen to [1.1.1]propellane. As used herein, "hydride source" is a reagent capable of donating a H⁻ or H-radical (H.). Suitable hydride sources can transfer a hydride to [1.1.1]propellane or the metal center of the Group VIII transition metal compound to give a metal-hydride complex.

In some embodiments, the hydride source can be a metal-based hydride source. Examples include, but are not limited to, alkali metal-based hydrides, and alkali metal-based borohydrides (such as, sodium borohydride, sodium cyanoborohydride, lithium borohydride and sodium triacetoxyborohydride). In other embodiments, the hydride source can be a non-metal-based hydride source. Examples of non-metal-based hydride sources include, but are not limited to, silanes (for example, phenylsilane and methyldiphenylsilane), 1,1,3,3-tetramethyldisiloxane (TMDSO) and an optionally substituted borane (such as, $BH_3$, $BH_3$-complex, 9-Borabicyclo[3.3.1]nonane (9-BBN), and isopinocampheylborane).

Hydride source reagents can be obtained from commercial vendors and/or prepared utilizing methods known to those skilled in the art. The deuterated equivalents can also be obtained from commercial vendors and/or prepared using commercially available reagents, for example, as described in Keinan et al., *J. Org. Chem.*, 1987, 52, 2576-2580 and Harvey et al., *J. Am. Chem. Soc.*, 1957, 79, 1437-1439, which are hereby incorporated by reference in their entirety. In some embodiments, a method provided herein can include adding a first portion of the hydride source and a second portion of a hydride source.

The amounts of [1.1.1]propellane, the Group VIII transition metal compound, the hydride source and the reagent capable of contributing all or a part of a substituent group can vary. In some embodiments, one or more of the [1.1.1] propellane, the Group VIII transition metal compound, the hydride source and the reagent capable of contributing all or a part of a substituent group can be in excess to another one or more of the aforementioned compounds. In some embodiments, the reagent capable of contributing all or a part of a substituent group can be in excess of [1.1.1]propellane and/or the hydride source. In other embodiments, the hydride source can be in excess of [1.1.1]propellane and/or the reagent capable of contributing all or a part of a substituent group. In still other embodiments, [1.1.1]propellane can be in excess of the hydride source and/or the reagent capable of contributing all or a part of a substituent group. The amount in excess can vary. For example, the amount in excess can be about 1.5 times or more, about 2 times or more, about 3 times or more, or about 4 times or more. In some embodiments, the amount of [1.1.1]propellane to the amount of hydride source can be in the range of about 0.75 equivalents to about 2 equivalents. In some embodiments, the amount of [1.1.1]propellane to the amount of hydride source can be in the range of about 1 equivalents to about 1.5 equivalents. In some embodiments, the amount of [1.1.1]propellane to the amount of the reagent capable of contributing all or a part of a substituent group can be in the range of about 0.8 equivalents to about 4 equivalents. In some embodiments, the amount of [1.1.1]propellane to the amount of the reagent capable of contributing all or a part of a substituent group can be in the range of about 1.2 equivalents to about 3 equivalents. In other embodiments, one or more of [1.1.1]propellane, the Group VIII transition metal compound, the hydride source and the reagent capable of contributing all or a part of a substituent group can be in approximately equal molar amounts to another one or more of the aforementioned compounds.

The order in which each of [1.1.1]propellane, the Group VIII transition metal compound, the hydride source and the reagent capable of contributing all or a part of a substituent group are combined can also vary. For example, the Group VIII transition metal compound can be combined with the reagent capable of contributing all or a part of a substituent group, followed by the addition of [1.1.1]propellane and the hydride source. Alternatively, [1.1.1]propellane can be added before the reagent capable of contributing all or a part of a substituent group.

Additional Compounds

In some embodiments, a method described herein can include one or more additional compounds. For example, a method described herein can also include an additional compound that can act as an initiator. An initiator can generate a reactive radical species to facilitate the reaction.

In some embodiments, a method described herein can also include a compound that can act as a trapping compound. As an example, a trapping compound can combine with a byproduct of one of the compounds formed in a method described herein and can reduce the number of side reaction(s) and/or the amount of side products formed during the reaction.

In some embodiments, a method described herein can also include an additional compound that can act as an additive. As used herein, an "additive" facilitates the regeneration of a reactive compound. For example, an additive can regenerate the reactive transition metal compound. Suitable additional compounds that can be used in a methods descried herein include, for example, tert-butyl hydroperoxide, benzoyl peroxide, di-tert-butyl peroxide, 2,2'-azobis(2-methylpropionitrile) (AIBN), methylmorpholine oxide, potassium hexacyanoferrate(III), oxygen, sodium periodate, silver bromoate, silver chloroformate, ceric ammonium nitrate, hydrogen peroxide, sodium hypochlorite, Oxone®, 3-chloroperbenzoic acid, and the like. An example of an additive is butylated hydroxytoluene (BHT).

One or more additional compounds can be included in a method provided herein at various points in a method described herein. Likewise, various amounts of one or more additional compounds can be included in a method provided herein. The timing and amounts of additional compounds to include in a methods provided herein is within the knowledge of those skilled in the art.

Solvents

A variety of solvents can be utilized in the methods described herein. In some embodiments, the solvent can be an alcohol-based solvent. In some embodiments, a co-solvent can be used in a method described herein. Suitable solvents and co-solvents include, but are not limited to, ethanol, methanol, isopropanol, $H_2O$, THF, NMP, DMF, DMSO, MTBE, $CH_3CN$, $CH_2Cl_2$, toluene, or dioxane, and mixtures thereof. In some embodiments, the solvent can be $H_2O$. In other embodiments, the solvent can be THF. In still other embodiments, the solvent can be ethanol. In yet still other embodiments, the solvent can be methanol. In some embodiments, the solvent can be $Et_2O$. In some embodiments, the co-solvent combination can be $H_2O$ and THF. In other embodiments, the co-solvent combination can be $Et_2O$ and MeOH. In some embodiments, the solvent can be isopropanol.

Time and Temperature

The methods provided herein can be conducted at various temperatures. Further, the temperature can be lowered and/or raised during the method. In some embodiments, the temperature can be in the range of about −5° C. to about 3° C. In some embodiments, the temperature can be room temperature (about 25° C.). In other embodiments, the temperature can be about 0° C. In some embodiments, the temperature can be greater 30° C. In other embodiments, the temperature can be less than 0° C.

The time can also vary for a method described herein. For example, the time of a method provided herein can be in the range of about 30 minutes to about 3 hours. In some embodiments, the time can be in the range of about 10 hours to about 24 hours. In some embodiments, the time can be in the range of about 8 hours to about 12 hours.

As provided herein, the $R^1$ that is first attached to the BCP can undergo further transformations to form other $R^1$ groups. For example, an $R^1$ group can be reduced using methods known to those skilled in the art to form other $R^1$ groups. Examples of further transformations include oxidation, addition, elimination, condensation, coupling, metathesis, hydrolysis, aminolysis, rearrangements, cyclizations, aromatization, annulations, fragmentations, substitutions, transfers, homologations, multicomponent reactions and combinations of any of the aforementioned. As a specific example, an azide can be reduced using methods known to those skilled in the art to form an amino group. Further examples of suitable transformations are provided in Richard C. Larock *Comprehensive Organic Transformations: A Guide to Functional Group Preparations* ($2^{nd}$ Ed., Wiley, John & Sons, Inc., November 1999); and Jerry March, (*Advanced Organic Chemistry: Reactions, Mechanisms, and Structure* ($6^{th}$ Ed., Wiley, John & Sons, Inc., January 2007).

Compounds

Some embodiments disclosed herein relate to a compound of Formula (I):

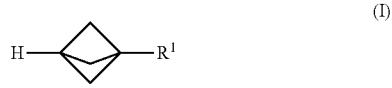

(I)

wherein: $R^1$ can be —$N_3$, halogen, —CN, —$CF_3$, —OH, —SCN, —NCO, —NO, —C(=$NOR^2$)(CN), —CH(=$NOR^2$), —COH, an optionally substituted $C_{1-30}$ alkyl, an optionally substituted $C_{2-30}$ alkenyl, an optionally substituted $C_{2-30}$ alkynyl, an optionally substituted cycloalkyl, an optionally substituted cycloalkenyl, an optionally substituted cycloalkynyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl), an optionally substituted alkoxy, an optionally substituted acyl, an optionally substituted amino, an optionally substituted alkoxyalkyl, an optionally substituted acylalkyl, an optionally substituted aminoalkyl, an optionally substituted hydroxyalkyl, an optionally substituted haloalkyl, an optionally substituted haloalkoxy, an optionally substituted arylthio, or an optionally substituted alkylthio; and $R^2$ can be ($C_1$ to $C_{10}$) alkoxy, an optionally substituted $C_{1-30}$ alkyl, an optionally substituted alkenyl, an optionally substituted alkynyl, an optionally substituted cycloalkyl, an optionally substituted cycloalkenyl, an optionally substituted cycloalkynyl, an optionally substituted aryl, an optionally substituted heteroaryl, an optionally substituted heterocyclyl, an optionally substituted aryl(alkyl), an optionally substituted heteroaryl(alkyl), an optionally substituted heterocyclyl(alkyl), an optionally substituted aminoalkyl or an optionally substituted alkylamino.

One or more methods described herein can be used to obtain a compound of Formula (I). For example, in some embodiments, $R^1$ can be —$N_3$, halogen, —$CF_3$, —CN, —$CF_3$, —OH, —SCN, —NCO, —NO, —C(=$NOR^2$)(CN), —CH(=$NOR^2$) or —CO. In some embodiments, one or more methods described herein can be used to obtain a compound of Formula (I), wherein $R^1$ can be -an optionally substituted $C_{1-30}$ alkyl, an optionally substituted $C_{2-30}$ alkenyl, an optionally substituted $C_{2-30}$ alkynyl, an optionally substituted cycloalkyl, an optionally substituted cycloalkenyl, an optionally substituted cycloalkynyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl), an optionally substituted alkoxy, an optionally substituted acyl, an optionally substituted amino, an optionally substituted alkoxyalkyl, an optionally substituted acylalkyl, an optionally substituted aminoalkyl, an optionally substituted hydroxyalkyl, an optionally substituted haloalkyl, an optionally substituted haloalkoxy, an optionally substituted arylthio, or an optionally substituted alkylthio.

In some embodiments, $R^1$ can be —$N_3$. In other embodiments, $R^1$ can be halogen (for example, F, Cl, Br and/or I). In still other embodiments, $R^1$ can be —CN. In some embodiments, $R^1$ can be —$CF_3$. In yet still other embodiments, $R^1$ can be OH. In some embodiments, $R^1$ can be —SCN. In other embodiments, $R^1$ can be —NCO. In still other embodiments, $R^1$ can be —NO. In yet still other embodiments, $R^1$ can be —C(=$NOR^2$)(CN) and/or —CH(=$NOR^2$). In some embodiments, $R^1$ can be —COH. In other embodiments, $R^1$ can be an optionally substituted $C_{1-30}$ alkyl. For example, $R^1$ can be an optionally substituted $C_{1-4}$ alkyl, such as —CH($CO_2$H)(NHBoc). In still other embodiments, $R^1$ can be an optionally substituted $C_{2-30}$ alkenyl. In yet still other embodiments, $R^1$ can be an optionally substituted $C_{2-30}$ alkynyl. In some embodiments, $R^1$ can be an optionally substituted cycloalkyl. In other embodiments, $R^1$ can be an optionally substituted cycloalkenyl. In still other embodiments, $R^1$ can be an optionally substituted cycloalkynyl. In yet still other embodiments, $R^1$ can be an optionally substituted aryl. In some embodiments, $R^1$ can be an optionally substituted heteroaryl. In other embodiments, $R^1$ can be an optionally substituted heterocyclyl. Examples of optionally substituted aryls, optionally substituted heteroaryls and optionally substituted heterocyclyls, include, but are not limited to, optionally substituted mono-cyclic aryls, optionally substituted mono-cyclic heteroaryls and optionally substituted mono-cyclic heterocyclyls, respectively. In still other embodiments, $R^1$ can be, an optionally substituted aryl($C_{1-6}$ alkyl). In yet still other embodiments, $R^1$ can be an optionally substituted heteroaryl($C_{1-6}$ alkyl). In some embodiments, $R^1$ can be an optionally substituted heterocyclyl($C_{1-6}$ alkyl). In other embodiments, $R^1$ can be an optionally substituted alkoxy. In still other embodiments, $R^1$ can be an optionally substituted acyl. In yet still other embodiments, $R^1$ can be an optionally substituted amino. In some embodiments. $R^1$ can be an optionally substituted alkoxyalkyl. In other embodiments. $R^1$ can be an optionally substituted acylalkyl. In still other embodiments, $R^1$ can be an optionally substituted aminoalkyl. In yet still other embodiments, $R^1$ can be an optionally substituted hydroxyalkyl. In some embodiments, $R^1$ can be an optionally substituted haloalkyl. In other embodiments, $R^1$ can be an optionally substituted haloalkoxy. In still other embodiments, $R^1$ can be an optionally substituted arylthio. In yet still other embodiments, $R^1$ can be an optionally substituted alkylthio. In some embodiments, $R^1$ can be an unsubstituted aminoalkyl. In some embodiments, $R^1$ can be a substituted aminoalkyl, such as —CH($NH_2$)($CO_2$H).

As provided herein, $R^2$ can be a variety of groups. For example, $R^2$ can be ($C_1$ to $C_{10}$) alkoxy, an optionally substituted $C_{1-30}$ alkyl, an optionally substituted alkenyl, an optionally substituted alkynyl, an optionally substituted cycloalkyl, an optionally substituted cycloalkenyl, an optionally substituted cycloalkynyl, an optionally substituted aryl, an optionally substituted heteroaryl, an optionally substituted heterocyclyl, an optionally substituted aryl(alkyl), an optionally substituted heteroaryl(alkyl), an optionally substituted heterocyclyl(alkyl), an optionally substituted aminoalkyl or an optionally substituted alkylamino. In some embodiments, $R^2$ can be an optionally substituted benzyl. In some embodiments, $OR^2$ can be carbimidoyl cyanide, carbaldehyde oxime, (benzyloxy) carbimidoyl cyanide or carbaldehyde O-benzyl oxime.

A non-limiting list of compounds of Formula (I) include the following:

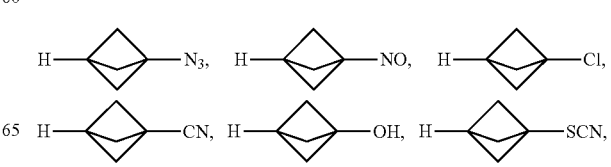

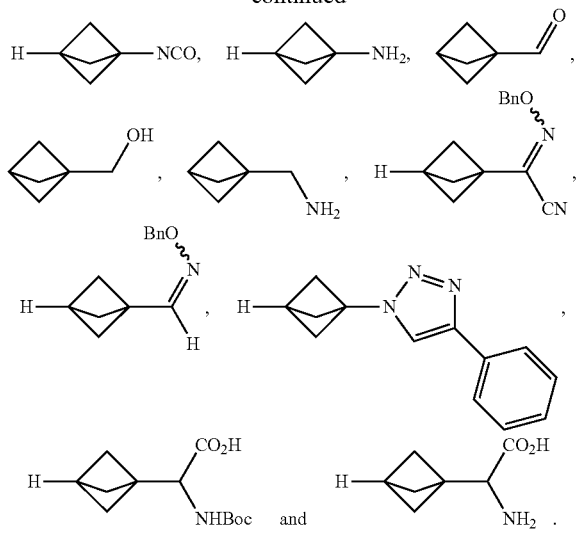

In some embodiments, $R^1$ cannot be —$N_3$. In other embodiments, $R^1$ cannot be halogen (for example, F, Cl, Br and/or I). In still other embodiments, $R^1$ cannot be —CN. In some embodiments, $R^1$ cannot be —$CF_3$. In yet still other embodiments, $R^1$ cannot be OH. In some embodiments, $R^1$ cannot be —SCN. In other embodiments, $R^1$ cannot be —NCO. In still other embodiments, $R^1$ cannot be —NO. In yet still other embodiments, $R^1$ cannot be —C(=$NOR^2$)CN) and/or —CH(=$NOR^2$). In some embodiments, $R^1$ cannot be —COH. In other embodiments, $R^1$ cannot be an optionally substituted $C_{1-30}$ alkyl. In still other embodiments, $R^1$ cannot be an optionally substituted $C_{2-30}$ alkenyl. In yet still other embodiments, $R^1$ cannot be an optionally substituted $C_{2-30}$ alkynyl. In some embodiments, $R^1$ cannot be an optionally substituted cycloalkyl. In other embodiments, $R^1$ cannot be an optionally substituted cycloalkenyl. In still other embodiments, $R^1$ cannot be an optionally substituted cycloalkynyl. In yet still other embodiments, $R^1$ cannot be an optionally substituted aryl. In some embodiments, $R^1$ cannot be an optionally substituted heteroaryl. In other embodiments, $R^1$ cannot be an optionally substituted heterocyclyl. In still other embodiments, $R^1$ cannot be, an optionally substituted aryl($C_{1-6}$ alkyl). In yet still other embodiments, $R^1$ cannot be an optionally substituted heteroaryl($C_{1-6}$ alkyl). In some embodiments, $R^1$ cannot be an optionally substituted heterocyclyl($C_{1-6}$ alkyl). In other embodiments, $R^1$ cannot be an optionally substituted alkoxy. In still other embodiments, $R^1$ cannot be an optionally substituted acyl. In yet still other embodiments, $R^1$ cannot be an optionally substituted amino. In some embodiments, $R^1$ cannot be an optionally substituted alkoxyalkyl. In other embodiments, $R^1$ cannot be an optionally substituted acylalkyl. In still other embodiments, $R^1$ cannot be an optionally substituted aminoalkyl. In yet still other embodiments, $R^1$ cannot be an optionally substituted hydroxyalkyl. In some embodiments, $R^1$ cannot be an optionally substituted haloalkyl. In other embodiments, $R^1$ cannot be an optionally substituted haloalkoxy. In still other embodiments, $R^1$ cannot be an optionally substituted arylthio. In yet still other embodiments, $R^1$ cannot be an optionally substituted alkylthio. In some embodiments, $R^1$ cannot be an unsubstituted $C_{1-30}$ alkyl. In some embodiments, $R^1$ cannot be an unsubstituted aminoalkyl. In some embodiments, $R^1$ cannot be a substituted aminoalkyl. In some embodiments, $R^1$ cannot be an optionally substituted In some embodiments, a compound of Formula (I) cannot be

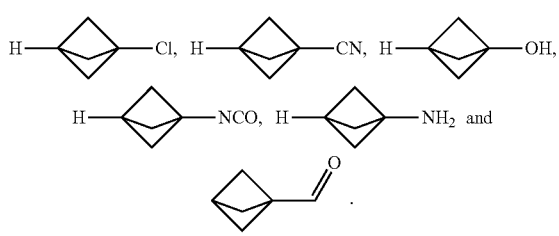

In other embodiments, a compound of Formula (I) cannot be

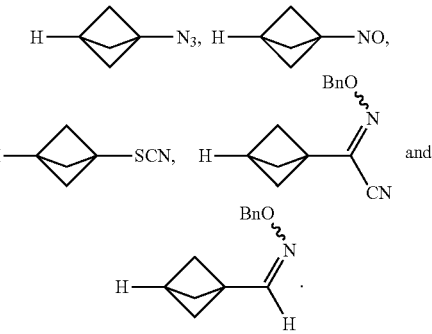

In still other embodiments, a compound of Formula (I) cannot be

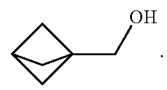

In yet still other embodiments, a compound of Formula (I) cannot be

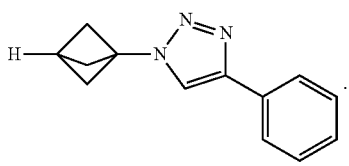 [SMILES: c1ccc(-c2cn(C34CC(C3)C4)nn2)cc1]

In some embodiments, a compound of Formula (I) cannot be

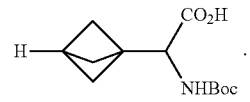

In other embodiments, a compound of Formula (I) cannot be

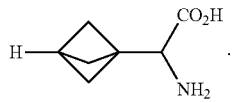

Additional details for preparing substituted bicyclo[1.1.1] pentane compounds are provided in Table 1.

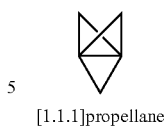 + [1.1.1]propellane →(Group VIII compound, reagent that includes R¹ or a portion of R¹, hydride source)→ 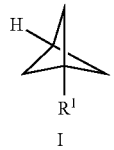

I

TABLE 1

| Reagent for R¹ | Group VIII compound | Hydride Source | Product |
|---|---|---|---|
| NaN$_3$ | Fe$_2$(ox$_3$)·6H$_2$O | NaBH$_4$ | H—◇—N$_3$ |
| NaNO$_2$ | Fe$_2$(ox$_3$)·6H$_2$O | NaBH$_4$ | H—◇—NO |
| TsCl | Fe$_2$(ox$_3$)·6H$_2$O | NaBH$_4$ | H—◇—Cl |
| TsCN | Fe$_2$(ox$_3$)·6H$_2$O | NaBH$_4$ | H—◇—CN |
| (EtO)$_2$P(O)CN | Fe$_2$(ox$_3$)·6H$_2$O | NaBH$_4$ | H—◇—CN |
| O$_2$ | Fe$_2$(ox$_3$)·6H$_2$O | NaBH$_4$ | H—◇—OH |
| KSCN | Fe$_2$(ox$_3$)·6H$_2$O | NaBH$_4$ | H—◇—SCN |
| KOCN | Fe$_2$(ox$_3$)·6H$_2$O | NaBH$_4$ | H—◇—NCO |
| PhSO$_2$C(CN)=N-OBn | Fe$_2$(ox$_3$)·6H$_2$O | NaBH$_4$ | H—◇—C(CN)=N-OBn |
| PhSO$_2$CH=N-OBn | Fe$_2$(ox$_3$)·6H$_2$O | NaBH$_4$ | H—◇—CH=N-OBn |
| R¹—C$_{2-10}$ alkenyl* | Fe(acac)$_3$ | PhSiH$_3$ | R¹—C$_{2-10}$ alkyl* |

TABLE 1-continued

| Reagent for R¹ | Group VIII compound | Hydride Source | Product |
|---|---|---|---|
| TsCN | Fe(acac)$_3$ | PhSiH$_3$ |  |
| †† | Fe(acac)$_3$ | PhSiH$_3$ | 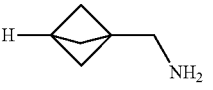 |
| †† | Fe(acac)$_3$ | PhSiH$_3$ | 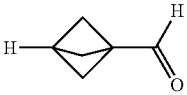 |
| †† | Fe(acac)$_3$ | PhSiH$_3$ | 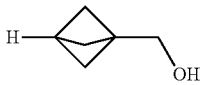 |
| †† | Fe(acac)$_3$ | PhSiH$_3$ | 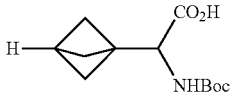 |
| †† | Fe(acac)$_3$ | PhSiH$_3$ | 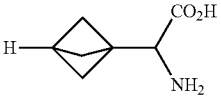 |
| 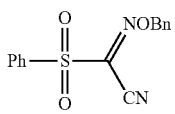 | Fe(acac)$_3$ | PhSiH$_3$ | 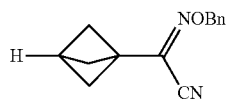 |
| 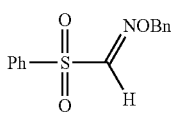 | Fe(acac)$_3$ | PhSiH$_3$ | 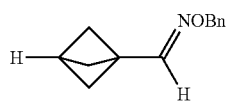 |
| TosN$_3$ | Fe(acac)$_3$ | PhSiH$_3$ | 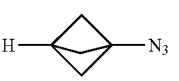 |
| †† | Fe(acac)$_3$ | PhSiH$_3$ | 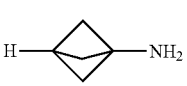 |
| †† | Fe(acac)$_3$ | PhSiH$_3$ | 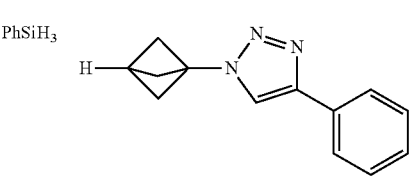 |

*indicates that the alkenyl and alkyl can be optionally substituted

††indicates the substituted product bicyclopentane was obtained after one or more further transformations of a substituted bicyclopentane produced from the conditions shown.

Scheme 3: Amine

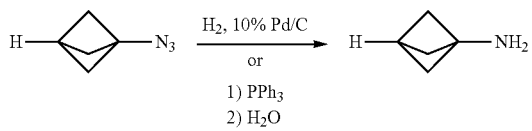

The reduction of 1-azidobicyclo[1.1.1]pentane can be carried out by one skilled in the arts, utilizing conditions such as hydrogenation (H₂, 10% Pd/C), transfer hydrogenation, or Staudinger reduction with triphenylphosphine and water [or conditions described in Richard C. Larock (supra)] can give 1-bicyclo[1.1.1]pentylamine (Scheme 3).

Scheme 4: Aldehyde

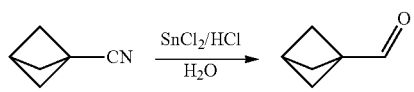

The reduction of bicyclo[1.1.1]pentane-1-carbonitrile with suitable chemical reagent [such as, as described in March (supra); (for example mild aluminum hydride reagents such as diisobutylaluminum hydride (DIBAL-H) followed with acidic aqueous conditions, or tin(II) chloride/HCl followed with acidic aqueous conditions (Stephen's reaction, and the like)] can give bicyclo[1.1.1]pentane-1-carbaldehyde (Scheme 4).

Scheme 5: Methylalcohol

Further reduction with an appropriate reagent (such as described by March (supra) and Larock (supra) (for example, LiAlH₄, NaBH₄, and the like)) can give bicyclo[1.1.1]pentan-1-ylmethanol (Scheme 5).

Scheme 6: Methylamine

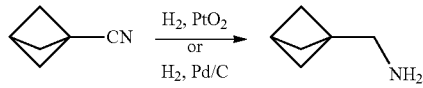

The reduction of bicyclo[1.1.1]pentane-1-carbonitrile is carried out with a suitable chemical reagent (such as described by March (supra) and Larock (supra) (for example, lithium aluminium hydride, palladium catalyst/hydrogen, platinum catalyst/hydrogen, Raney nickel/hydrogen, diborane, and the like)) can give bicyclo[1.1.1]pentan-1-ylmethanamine (Scheme 6).

It should be noted that one skilled in the art would know how to modify the procedures set forth in the illustrative schemes and examples to arrive at the desired products.

EXAMPLES

Example 1: General Procedure

A solution of Fe(acac)₃ (30 mol % or 50 mol %) in anhydrous EtOH, anhydrous MeOH, or a ~2:1 mixture of anhydrous MeOH and anhydrous Et₂O containing 1 ppm BHT (10 mM final concentration) was prepared and stirred under N₂ for 2 mins. [1.1.1]Propellane (1 equiv. as a solution in Et₂O) and the appropriate reagent capable of contributing all or a part of a substituent group (1.2-3 equiv.) were added followed by PhSiH₃ (1.0-1.5 equiv.). After stirring overnight at room temperature (RT), the mixture containing the product was concentrated to afford the desired compound that was either further purified by flash chromatography on silica gel or the product was carried forward without isolation or purification to generate a corresponding derivative.

Example 2: bicyclo[1.1.1]pentane-1-carbonitrile

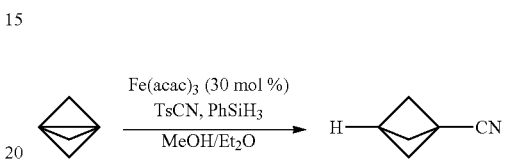

Bicyclo[1.1.1]pentane-1-carbonitrile was prepared according to the general procedure, using 4-methylbenzenesulfonyl cyanide (TsCN) as the appropriate reagent capable of contributing all or a part of a substituent group. $^1$H NMR (400 MHz, MeOH-d₄) δ 2.40 (s, 1H), 2.31 (s, 6H).

Example 3: bicyclo[1.1.1]pentane-1-ylmethanamine

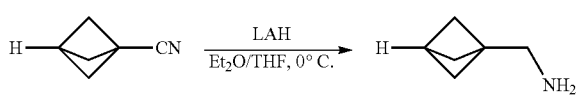

Bicyclo[1.1.1]pentan-1-ylmethanamine was prepared by dissolving Bicyclo[1.1.1]pentane-1-carbonitrile in anhydrous Et₂O (0.090 M) and cooling to 0° C. A 2 M solution of LAH in THF (5.3 equiv.) was added dropwise with stirring. After 30 mins, the solution was quenched at 0° C. by the addition of EtOAc (2 mL). The mixture was concentrated to 30% of its original volume and loaded onto a column of Si-Tosic acid resin. MeOH was flushed through the column followed by elution of the desired compound with 1N NH₃ in MeOH. Concentration of the solution to 10% of its original volume followed by acidification with 4N HCl in dioxane and concentration to dryness afforded bicyclo[1.1.1]pentan-1-ylmethanamine. $^1$H NMR (400 MHz, MeOH-d₄) δ 2.97 (s, 2H), 2.57 (s, 1H), 1.90 (s, 6H); LC/MS (APCI) m/z 98.1 [C₆H₁₁N+H]⁺.

Example 4: bicyclo[1.1.1]pentane-1-carbaldehyde

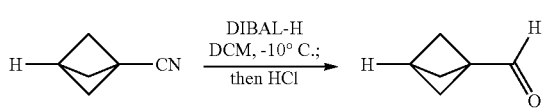 [SMILES: N#CC12CC(C1)C2 ; "then HCl" ; O=CC12CC(C1)C2]

A solution of bicyclo[1.1.1]pentane-1-carbonitrile (1.0 equiv.) in DCM (0.3 M) was cooled to −10° C. and treated with a 1.0 M solution of DIBAL-H (1.4 equiv.). After 2 h, the solution was quenched at −10° C. with 1N HCl and allowed to stir for 10 mins at RT. A 10% aqueous solution of Rochelle's salt was added, and the mixture was stirred until a clear separation of layers occurred. The mixture was extracted with DCM (4×), and the combined organics were dried (Na$_2$SO$_4$) then concentrated to afford bicyclo[1.1.1]pentane-1-carbaldehyde. $^1$H NMR (400 MHz, CDCl$_3$) δ 9.48 (s, 1H), 2.53 (s, 1H), 2.08 (s, 6H).

Example 5: bicyclo[0.1.11]pentane-1-ylmethanol

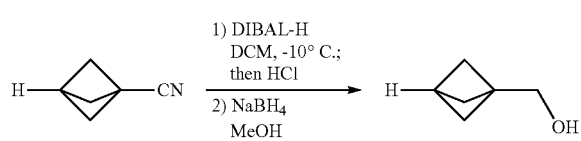 [SMILES: N#CC12CC(C1)C2 ; OCC12CC(C1)C2]

Bicyclo[1.1.1]pentane-1-carbaldehyde was prepared as described herein in Example 4. Bicyclo[1.1.1]pentane-1-carbaldehyde was re-dissolved in MeOH (0.3 M) and cooled to 0° C. NaBH$_4$ (1.2 equiv.) was added in one portion, and the suspension was allowed to warm to RT. The mixture was stirred for 1 h and monitored by $^1$H NMR spectroscopy. The mixture was quenched by the addition of H$_2$O and extracted with Et$_2$O. The combined organics were dried (Na$_2$SO$_4$) and concentrated to afford bicyclo[1.1.1]pentane-1-ylmethanol as an oil. $^1$H NMR (400 MHz, CDCl$_3$) δ 3.70 (s, 2H), 2.53 (s, 1H), 1.74 (s, 6H).

Example 6: 2-(bicyclo[1.1.1]pentan-1-yl)-2-((tert-butoxycarbonyl)amino)acetic acid

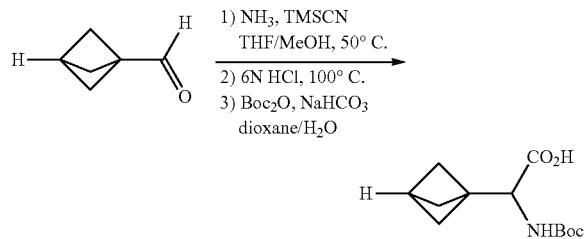

A crude solution of bicyclo[1.1.1]pentane-1-carbaldehyde (1 equiv.) in THF (0.6 M) at 0° C. was treated with a 7 N solution of ammonia (15 equiv.) in MeOH. The solution was then treated with TMSCN (1.5 equiv.), and the resulting mixture was stirred at 50° C. until complete. Once complete, the mixture was cooled to RT and concentrated to dryness. The residue was re-dissolved in aqueous 6N HCl (0.3 M) then heated to 100° C. for 4.5 h. The mixture was cooled to RT and quenched by the addition of solid NaHCO$_3$ until basic by pH paper. The solution was further diluted with sat. aq. NaHCO$_3$ and dioxane (2:1). Boc-anhydride (1.2 equiv.) was added, and the mixture was stirred at RT overnight. The mixture was acidified with 1N HCl and extracted with EtOAc (4×). The combined organics were dried (Na$_2$SO$_4$) and concentrated to afford a dark oil, which was further purified by reverse phase chromatography (ISCO C18, H$_2$O w/0.1% formic acid/ACN w/0.1% formic acid) to provide 2-(bicyclo[1.1.1]pentan-1-yl)-2-((tert-butoxycarbonyl)amino)acetic acid as a white powder. The product exists in solution as a 5.5:1 mixture of rotamers. Major rotamer: $^1$H NMR (400 MHz, DMSO-d6) δ 12.44 (s, COOH, 1H), 6.94 (d, J=8.0 Hz, 1H), 3.90 (d, J=8.0 Hz, 1H), 2.44 (s, 1H), 1.77-1.67 (m, 6H), 1.38 (s, 9H); LC/MS (APCI) m/z 142.1 [C$_{12}$H$_{19}$NO$_4$—C$_5$H$_9$O$_2$+H]$^+$.

Example 7: 2-amino-2-(bicyclo[1.1.1]pentan-1-yl)acetic acid hydrogen chloride

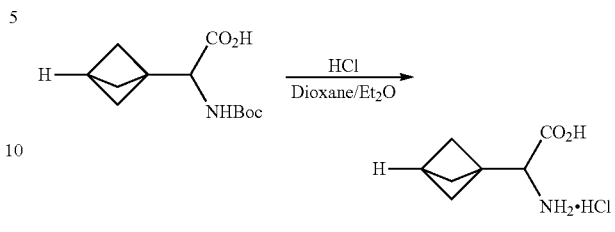

A solution of 2-(bicyclo[1.1.1]pentan-1-yl)-2-((tert-butoxycarbonyl)amino)acetic acid (1 equiv.) in ethyl acetate (0.2 M) was treated with a 4N HCl (10 equiv.) in dioxane. The mixture was stirred overnight. Once complete (as monitored by LCMS), the mixture was concentrated under reduced pressure and triturated with Et$_2$O to afford 2-amino-2-(bicyclo[1.1.1]pentan-1-yl)acetic acid hydrogen chloride as a white solid. $^1$H NMR (400 MHz, DMSO-d$_6$) δ 13.75 (br s, COOH, 1H), 8.32 (br s, NH, 3H), 3.93 (s, 1H), 2.50 (s, 1H), 1.85-1.78 (m, 6H); LC/MS (APCI) m/z 142.1 [C$_7$H$_{11}$NO$_2$+H]$^+$.

Example 8: (Z)—N-(benzyloxy)bicyclo[1.1.1]pentane-1-carbimidoyl cyanide

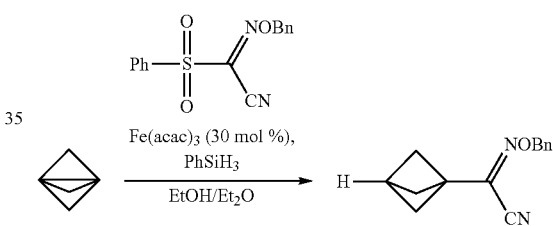

(Z)—N-(benzyloxy)bicyclo[1.1.1]pentane-1-carbimidoyl cyanide was prepared according to the general procedure, with (E)-N-(benzyloxy)-1-(phenylsulfonyl)methanimidoyl cyanide as the appropriate reagent capable of contributing all or a part of a substituent group. The product was isolated as a mixture of isomers (E/Z). Major isomer: $^1$H NMR (400 MHz, CDCl$_3$) δ 7.40-7.30 (m, 5H), 5.25 (s, 2H), 2.55 (s, 1H), 2.08 (s, 6H). Minor isomer $^1$H NMR (400 MHz, CDCl$_3$) δ 7.40-7.30 (m, 5H), 5.22 (s, 2H), 2.51 (s, 1H), 2.19 (s, 6H).

Example 9: (E)-bicyclo[1.1.1]pentane-1-carbaldehyde O-benzyl oxime

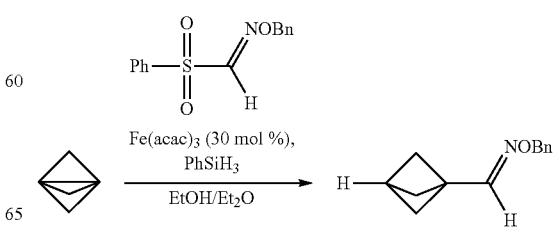

(E)-bicyclo[1.1.1]pentane-1-carbaldehyde O-benzyl oxime was prepared according to the general procedure with (E)-(phenylsulfonyl)methanal O-benzyl oxime as the appropriate reagent capable of contributing all or a part of a substituent group. LC/MS (APCI) m/z 202.1 $[C_{13}H_{15}NO+H]^+$.

Example 10: 1-azidobicyclo[1.1.1]pentane and bicyclo[1.1.1]pentan-1-amine

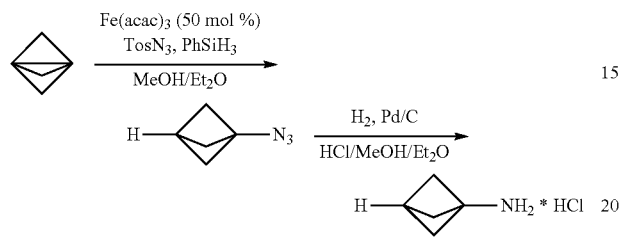

1-azidobicyclo[1.1.1]pentane was prepared according to the general procedure with tosylazide as the appropriate reagent capable of contributing all or a part of a substituent group. To the crude azide in MeOH/Et$_2$O was added HCl (37% aqueous, 1.2 equiv.) followed by Pd/C (20 mol %). The mixture was stirred under a H$_2$ atmosphere overnight. The mixture was concentrated to dryness, and then separated between EtOAc and H$_2$O. The aqueous layer was made basic and then extracted with EtOAc. The organic layer was acidified with 4N HCl in dioxane. The mixture was concentration to dryness and afforded bicyclo[1.1.1]pentan-1-amine. Bicyclo[1.1.1]pentan-1-amine: LC/MS (APCI) m/z 84.1 $[C_5H_9N+H]^+$.

Example 11: 1-azidobicyclo[1.1.1]pentane and 1-(bicyclo[1.1.1]pentan-1-yl)-4-phenyl-1H-1,2,3-triazole

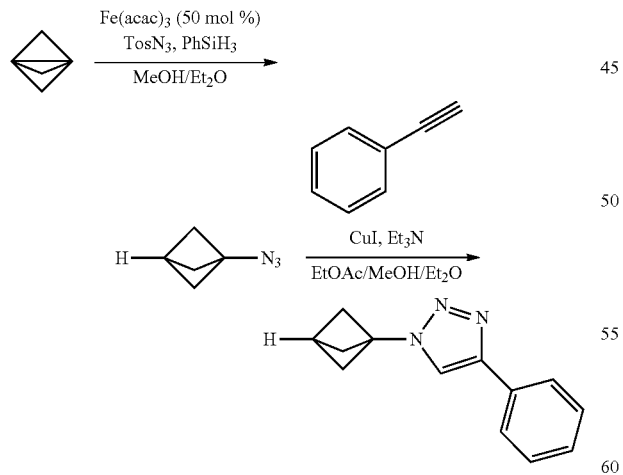

1-azidobicyclo[1.1.1]pentane was prepared as described herein in Example 10. Following the completion of the reaction, EtOAc and H$_2$O were added. The organic layer was the separated. To the organic layer containing the crude azide was added CuI (20 mol %), phenylacetylene (1.5 equiv.), and then Et$_3$N (2 equiv.). After 16 h, the reaction was concentrated to dryness and then purified by column chromatography to afford 1-(bicyclo[1.1.1]pentan-1-yl)-4-phenyl-1H-1,2,3-triazole. H NMR (400 MHz, CDCl$_3$) δ 7.84-7.82 (m, 2H), 7.74 (s, 1H), 7.45-7.40 (m, 2H), 7.35-7.30 (m, 1H), 2.74 (s, 1H), 2.44 (s, 6H); LC/MS (APCI) m/z 212.10 $[C_{13}H_{13}N_3+H]^+$.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:
1. A compound having the structure of Formula (I):

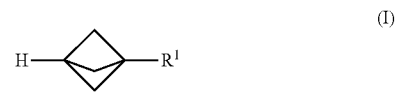

(I)

wherein:
$R^1$ is —N$_3$, —SCN, —NO, —C(=NOR$^2$)(CN), —CH(=NOR$^2$), CH(CO$_2$H)(NHBoc), —CH(CO$_2$H)(NH$_2$), an optionally substituted cycloalkynyl, an optionally substituted heteroaryl(C$_{1-6}$ alkyl), an optionally substituted heterocyclyl(C$_{1-6}$ alkyl), an optionally substituted aminoalkyl or an optionally substituted haloalkoxy; and
$R^2$ is (C$_1$ to C$_{10}$) alkoxy, an optionally substituted C$_{1-30}$ alkyl, an optionally substituted alkenyl, an optionally substituted alkynyl, an optionally substituted cycloalkyl, an optionally substituted cycloalkenyl, an optionally substituted cycloalkynyl, an optionally substituted aryl, an optionally substituted heteroaryl, an optionally substituted heterocyclyl, an optionally substituted aryl(alkyl), an optionally substituted heteroaryl(alkyl), an optionally substituted heterocyclyl(alkyl), an optionally substituted aminoalkyl or an optionally substituted alkylamino;
wherein an optionally substituted aminoalkyl is a NH$_2$ group connected, as a substituent, via a lower alkylene group; and
wherein the optionally substituted aminoalkyl is a straight-chained —CH$_2$— tethering group, forming bonds to connect molecular fragments via its terminal carbon atoms and wherein the lower alkylene group can be substituted by replacing one or more hydrogen of the lower alkylene group or by substituting both hydrogens on the same carbon with a cycloalkyl group.
2. The compound of claim 1, wherein the compound is

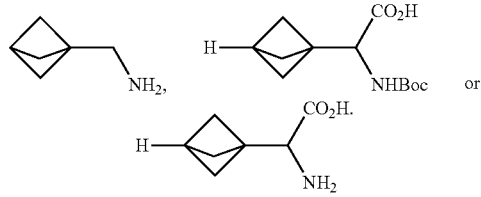

3. The compound of claim 1, wherein $R^1$ is a substituted aminoalkyl.

4. The compound of claim 1, wherein $R^1$ is an unsubstituted aminoalkyl.

5. The compound of claim 1, wherein $R^1$ is $H_2N-(CH_2)_n-$, wherein n is an integer in the range of 1 to 6.

6. The compound of claim 5, wherein n is 1.

7. The compound of claim 5, wherein n is 2.

8. The compound of claim 5, wherein n is 3.

9. The compound of claim 5, wherein n is 4.

10. The compound of claim 5, wherein n is 5.

11. The compound of claim 1, wherein the compound is

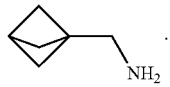

12. The compound of claim 1, wherein the compound is

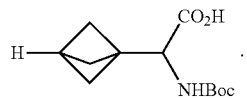

13. The compound of claim 1, wherein the compound is

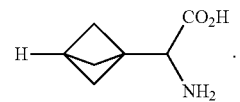

* * * * *

UNITED STATES PATENT AND TRADEMARK OFFICE
CERTIFICATE OF CORRECTION

PATENT NO. : 10,654,812 B2
APPLICATION NO. : 15/123898
DATED : May 19, 2020
INVENTOR(S) : Kevin Duane Bunker Page 1 of 2

It is certified that error appears in the above-identified patent and that said Letters Patent is hereby corrected as shown below:

On the Title Page

Column 2, item (57), Abstract, Lines 2-3, delete "bicyclo[1.1.1 jpentanes." and insert --bicyclo[1.1.1]pentanes.--.

On page 2, Column 2, item (56), Other Publications, Line 22, delete "carboxamidef'" and insert --carboxamide"--.

In the Specification

Column 2, Line 11, delete "Sziemes" and insert --Szeimies--.

Column 2, Line 27, delete "Left." and insert --Lett.--.

Column 3, Line 1, delete "herein." and insert --herein,--.

Column 5, Line 29, delete "heteroalicyclylic" and insert --heteroalicyclic--.

Column 5, Line 33, delete "tetrahydro-2H-pyran-4-yl)methyl," and insert --(tetrahydro-2H-pyran-4-yl)methyl,--.

Column 6, Line 47, delete "herein." and insert --herein,--.

Column 8, Line 59, delete "phthalocyanine." and insert --phthalocyanine,--.

Column 10, Line 12, delete "propellane" and insert --[1.1.1]propellane--.

Column 10, Line 34, delete "alkenyl" and insert --alkenyl.--.

Column 10, Line 38, delete "(H.)." and insert --(H·).--.

Signed and Sealed this
Twenty-ninth Day of September, 2020

Andrei Iancu
*Director of the United States Patent and Trademark Office*

CERTIFICATE OF CORRECTION (continued)
U.S. Pat. No. 10,654,812 B2

Column 10, Line 66, delete "[1.1.1.]propellane," and insert --[1.1.1]propellane--.

Column 12, Lines 1-2, delete "bromoate," and insert --bromate,--.

Column 12, Line 37, delete "3°" and insert --30°--.

Column 13, Line 42, delete "—NO." and insert -- —NO,--.

Column 13, Line 45, delete "-an" and insert --an--.

Column 14, Line 30 (approx.), delete "embodiments." and insert --embodiments,--.

Column 14, Line 31 (approx.), delete "embodiments." and insert --embodiments,--.

Column 15, Line 31, delete "—C(=NOR$^2$)CN)" and insert -- —C(=NOR$^2$)(CN)--.

Column 19, Table 1-continued, Line 15 (approx.), delete "††indicates" and insert --†† indicates--.

Column 21, Line 25 approx., delete "(for example" and insert --for example--.

Column 23, Line 6, delete "[0.1.11]" and insert --[1.1.1]--.

Column 23, Line 64, delete "d6)" and insert --d$_6$)--.

Column 24, Line 48, delete "isomer" and insert --isomer:--.

Column 25, Line 24, delete "tosylazide" and insert --tosyl azide--.

Column 26, Line 3, delete "H NMR" and insert --$^1$H NMR--.